US012778492B2

(12) United States Patent
Benway et al.

(10) Patent No.: US 12,778,492 B2
(45) Date of Patent: Nov. 3, 2026

(54) CLINICAL SPEECH ANALYSIS SYSTEM FOR CHILDHOOD SPEECH DISORDERS

(71) Applicants: Nina Benway, Clifton Park, NY (US); Jonathan Preston, Jamesville, NY (US); Asif Salekin, Syracuse, NY (US)

(72) Inventors: Nina Benway, Clifton Park, NY (US); Jonathan Preston, Jamesville, NY (US); Asif Salekin, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 130 days.

(21) Appl. No.: 18/599,837

(22) Filed: Mar. 8, 2024

(65) Prior Publication Data

US 2024/0298963 A1 Sep. 12, 2024

Related U.S. Application Data

(60) Provisional application No. 63/450,762, filed on Mar. 8, 2023.

(51) Int. Cl.

| | |
|---|---|
| ***G10L 15/16*** | (2006.01) |
| ***A61B 5/00*** | (2006.01) |
| ***G10L 15/22*** | (2006.01) |
| ***G10L 25/15*** | (2013.01) |
| ***G10L 25/18*** | (2013.01) |
| ***G10L 25/66*** | (2013.01) |
| ***G16H 50/20*** | (2018.01) |

(52) U.S. Cl.

CPC .......... *A61B 5/4803* (2013.01); *A61B 5/7267* (2013.01); *G10L 15/16* (2013.01); *G10L 15/22* (2013.01); *G10L 25/15* (2013.01); *G10L 25/18* (2013.01); *G10L 25/66* (2013.01); *G16H 50/20* (2018.01); *A61B 2503/06* (2013.01); *G10L 2015/225* (2013.01)

(58) Field of Classification Search

CPC . A61B 5/4803; A61B 5/7267; A61B 2503/06; G10L 15/16; G10L 15/22; G10L 25/15; G10L 25/18; G10L 25/66; G10L 2015/225; G10L 25/60; G10L 25/30; G16H 50/20; G09B 19/04

See application file for complete search history.

(56) References Cited

U.S. PATENT DOCUMENTS

| | | | | |
|---|---|---|---|---|
| 10,478,111 | B2 * | 11/2019 | Knoth | G10L 17/26 |
| 11,344,225 | B2 * | 5/2022 | Zigel | A61B 5/7278 |
| 2016/0284347 | A1 * | 9/2016 | Sainath | G06N 3/045 |

(Continued)

*Primary Examiner* — Abul K Azad

(74) *Attorney, Agent, or Firm* — David L. Nocilly; Bond Schoeneck & King PLLC

(57) ABSTRACT

A speech analysis system that can accurately determine whether a predetermined sound in a spoken work has been correctly pronounced. The speech analysis system includes a machine learning algorithm that has been trained to consider temporal and spectral information about the frame-by-frame components of a target sound. The speech analysis system is personalized based on previous therapy recordings for a speaker's specific error and correct/mispronounced exemplars from speakers with matched vocal tracts. The speech analysis system may be integrated into an adaptive therapy program, such as Speech Motor Chaining, to provide an assessment of proper speech and personalized biofeedback in the place of a live clinician.

12 Claims, 1 Drawing Sheet

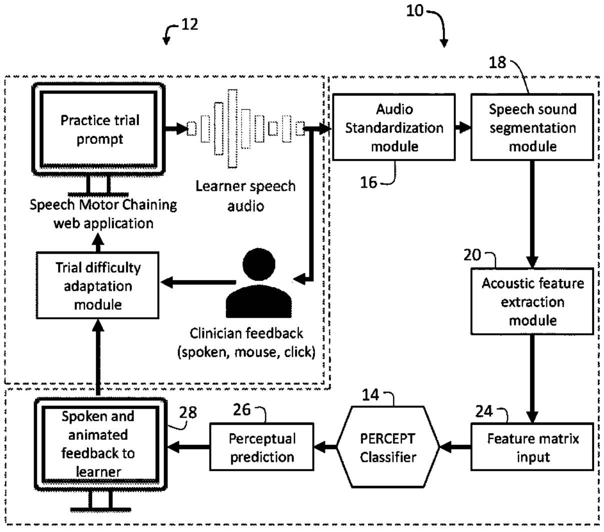

(56) References Cited

U.S. PATENT DOCUMENTS

| | | | | |
|---|---|---|---|---|
| 2016/0307576 | A1* | 10/2016 | Fuchs | G10L 19/0017 |
| 2021/0361227 | A1* | 11/2021 | Chou | G10L 25/66 |
| 2022/0415308 | A1* | 12/2022 | Berisha | G10L 15/30 |

* cited by examiner

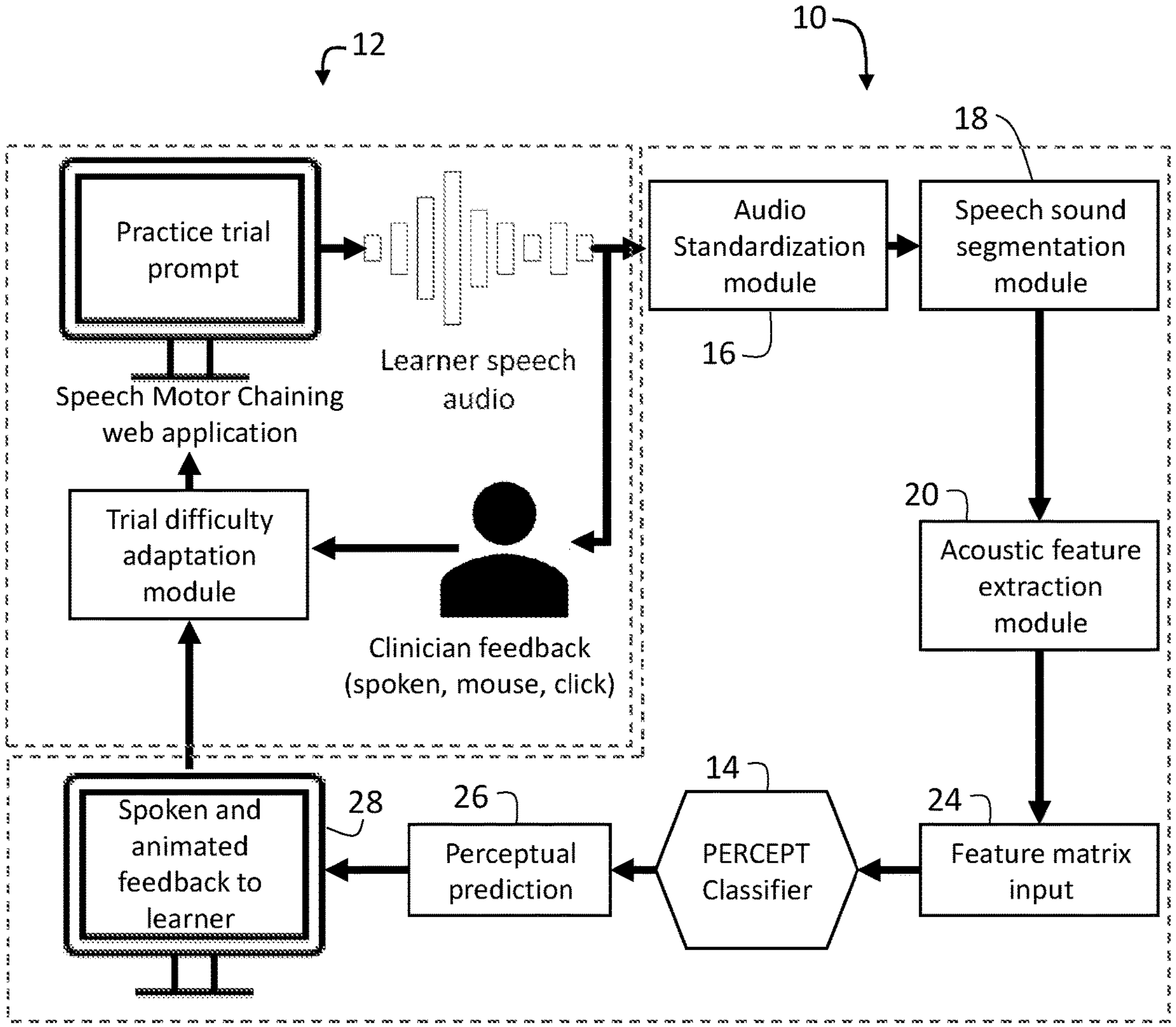
10
12
18
Practice trial prompt
Audio Standardization module
Speech sound segmentation module
16
Learner speech audio
Speech Motor Chaining web application
20
Trial difficulty adaptation module
Acoustic feature extraction module
Clinician feedback (spoken, mouse, click)
14
28
26
24
Spoken and animated feedback to learner
Perceptual prediction
PERCEPT Classifier
Feature matrix input

CLINICAL SPEECH ANALYSIS SYSTEM FOR CHILDHOOD SPEECH DISORDERS

CROSS-REFERENCE TO RELATED APPLICATION

The present application claims priority to U.S. Provisional Application No. 63/450,762, filed on Mar. 8, 2023, hereby incorporated by reference in its entirety.

STATEMENT REGARDING FEDERAL SUPPORT

This invention was made with government support under Grant No. 3R01DC017476 awarded by the National Institutes of Health (NIH). The government has certain rights in the invention.

BACKGROUND OF THE INVENTION

1. Field of the Invention

The present invention relates to speech analysis systems and, more specifically, to a machine learning based approach for mispronunciation detection of a target sound in the context of speech sound disorders.

2. Description of the Related Art

Speech sound disorders-difficulty producing the sounds in words accurately—can impact children's ability to be understood. Speech disorders can affect what children might eventually achieve academically, socially, occupationally, and financially as adults. The profound impact of speech sound disorders has recently risen to international prominence through Amanda S. C. Gorman, the Youth Poet Laureate of the United States. Gorman revealed that the speech sound /r/ was once the "bane of [her] human existence", and that she rewrote her poetry to only include words without /r/. She worked diligently to perfect her /r/ and ultimately gained confidence to say aloud words such as "poetry", "girl", and "world". This experience is unfortunately common: residual speech errors (RSE)—an unresolving subtype of speech sound disorder most frequently impacting /r/—affect an estimated 9% of American fourth grade children. Gorman's recitation of "The Hill We Climb" might have been less impactful if she did not recite her poem with articulate speech, and her success demonstrates what is possible when those with RSE practice intensely with skilled speech-language pathologists. Many with RSE, however, are not as successful as Gorman. While therapy can improve speech sound production, RSEs are notoriously difficult to treat. Furthermore, a sufficient amount of skilled therapy with a speech-language pathologist is not available to everyone who needs it because of large caseloads, insurance exclusions, and provider shortages. For these reasons, RSEs persist into adulthood for at least 1-2% of Americans. Computerized treatments with speech analysis could help children achieve sufficiently intense speech therapy, but there are currently no existing speech analysis tools that can adequately analyze a child's speech, determine whether a particular speech sound is produced correctly or incorrectly, and provide feedback to the child on the accuracy of their production using an adaptive, theoretically driven approach.

BRIEF SUMMARY OF THE INVENTION

The present invention provides a speech analysis system that can accurately determine whether a predetermined sound in a spoken word has been correctly pronounced, i.e., whether a listener would just such pronunciation to be correct or incorrect. More specifically, the speech analysis system includes a machine learning algorithm that can process information about a spoken sound from an audio file to determine whether a target speech sound was pronounced correctly. A recorded audio file may be processed to locate the desired sound to be assessed. Temporal or spectral information from the located sound may then be extracted and normalized. The normalized temporal or spectral information may then be processed by the machine learning algorithm. The machine learning algorithm may be trained to consider Mel-frequency cepstral coefficients as well as formant structure, vocal tract gesture estimation, spectral image information, and self-supervised learning speech representation, and may have the number of independent variables reduced by feature selection. The speech analysis system may be integrated into a therapy program, such as the Speech Motor Chaining treatment approach, to provide an assessment of proper speech and automate control of an adaptive speech therapy practice session in the place of a live clinician.

In a first embodiment, a system for providing real-time detection and analysis of speech sounds according to the present invention may comprise an input configured to receive an electronic audio file containing a target speech sound and a processor coupled to the input and programmed with a machine learning algorithm that has been trained with a predetermined data set to determine whether the target speech sound in the electronic audio file has been accurately pronounced and to output a signal reflecting the determination whether the target sound was accurately pronounced. The processor may be further programmed to receive an audio file containing the target speech sound and a text transcript of the audio file contents. The processor may be further programmed to locate the target speech sound within the audio file. The processor may be further programmed to extract a plurality of temporal and spectral features from the target speech sound. The plurality of spectral features may include at least one format, Mel-frequency cepstral coefficient, vocal tract gesture estimation, spectral image information, and elf-supervised learning speech representation. The plurality of temporal and spectral features may include at least one inter-format distance. The plurality of temporal and spectral features may include correctly pronounced and mispronounced exemplars from vocal tract-matched peers. The processor may be programmed to normalize the plurality of spectral features by z-standardizing according to age and sex specific acoustic values. The machine learning algorithm may select from the group consisting of a bidirectional long short-term memory recurrent neural network, convolutional neural networks, transformer neural networks, attention mechanisms, encoder/decoder neural networks, and temporal convolutional neural networks. The machine learning algorithm may comprise more than one algorithm selected from the group consisting of a bidirectional long short-term memory recurrent neural network, convolutional neural networks, transformer neural networks, attention mechanisms, encoder/decoder neural networks, and temporal convolutional neural networks. The processor may be further programmed to perform feature selection of the plurality of temporal or spectral features to reduce a number of independent variables. The predetermined data set may have included a series of desired sound tokens from speakers having different ages and different sexes as well as labels indicating human perceptual judgment of the sound tokens.

In another embodiment according to the present invention, a method of providing speech analysis comprises the steps of receiving an electronic audio file containing a target speech sound, processing the electronic audio file with a machine learning algorithm that has been trained with a predetermined data set to determine whether the target speech sound in the electronic audio file has been accurately pronounced, and outputting a signal reflecting the determination whether the target sound was accurately pronounced. The method may further comprise the step of locating the target speech sound within the audio file. The method may further comprise the step of extracting a plurality of spectral features of the target speech sound. The method may further comprise the step of performing feature selection of the plurality of spectral features to reduce a number of independent variables.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a schematic of a PERCEPT engine according to the present invention.

DETAILED DESCRIPTION OF THE INVENTION

Referring to the figures, wherein like numerals refer to like parts throughout, there is seen in FIG. 1 a real-time speech analysis system 10 according to the present invention that can classify correct and mispronounced speech sounds to provide automated feedback and enhance therapies directed toward addressing speech disorders. For example, system 10 is illustrated as being incorporated into a fully computerized treatment program 12 (illustrated as the Speech Motor Chaining approach) to provide accuracy feedback on speech sounds, such as /r/ and /s/, in the same generally way a clinician would do when implementing a partially computerized treatment program 12.

System 10 may be used to improve and facilitate speech therapy, which employs a theoretically motivated practice structure based on well-established motor learning principles. The conventional approach to performing a partially computerized treatment program 12 involves program 12 delivering a practice prompt, accepting a correct/incorrect rating of the child's production accuracy from a clinician, delivering of feedback, and then prompting the next trial with complexity driven based on the child's prior accuracy. Specifically, program 12 selects the words and phrases to be practiced. Program 12 then facilitates practice for the clinician by controlling the order and grouping of words/phrases within the practice trials. The existing software of program 12 also controls the type and frequency of motor-learning feedback that is assigned to that trial. It adapts these aspects in real-time according to the difficulty level that best promotes learning for the child. It is traditionally the job of the clinician to listen to the word spoken by the child and key an accuracy rating into the software. The existing software then prompts the clinician to deliver a specific type of clinical feedback, at a frequency customized based on the child's level within the program.

As seen in FIG. 1, system 10 can replace the clinician and automatically provide the accuracy rating needed by a more fully computerized treatment program 12. With system 10 incorporated, children will be able to practice improving their speech using program 12 with clinical-level feedback even on days that they are unable to access a clinician. The feedback may additionally be used to tailor training provided to the user, e.g., by providing specific information that can be used to trigger animations that specifically address the nature of the mistake being made that leads to the feedback that the pronunciation is incorrect.

System 10 comprises an input for receiving and processing an audio file 16 containing at least one target sound captured during a therapy session according to a standard format. Audio file 16 may comprise an uncompressed .wav file recorded in response to an electronic prompt to the user. For example, the recording could be launched during use of treatment program 12.

System 10 includes a speech sound segmentation module 18 programmed to locate the target sound within a spoken word captured in audio file. Conventional algorithms for locating voice activity may be used to identify the portion of the .wav file that contains the speaker's speech. Conventional algorithms for locating a target sound may be used to identify the portion of the .wav file that contains the target sound.

Next, system 10 is programmed to extract acoustic features 20 such as temporal and spectral information related to the located target sound from the relevant portion of the .wav file, which should include a tolerance before and after the located sound. The extracted temporal and spectral information may include the three formants, F1, F2, and F3, and well as inter-formant distances, such as F3-F2. The extracted temporal and spectral information may also include vocal tract gesture estimates: lip aperture, lip position, tongue tip constriction location, tongue tip constriction degree, tongue body constriction location, tongue body constriction degree, periodicity, aperiodicity, and pitch. The extracted temporal and spectral information may also include self-supervised learning speech x-vectors. Existing analysis software such as Praat To Formant (robust), the Speech Inversion System, and HuggingFace Wav2Vec2 may be used for this aspect of system 10.

Formants may be estimated using the Praat Formant (robust) function. Useful settings for the formant extraction include setting the time step(s) at 0.005; the time between centers of consecutive analysis frames. For every 1 second there will be 200 analysis frames of length (window length). The maximum number of formants may be set at 5, which is the number of formants extracted in the formant search frame. The formant ceiling (Hz) is a speaker specific value that describes the maximum frequency of the formant search frame. The window length may be set at 0.025, which is one-half of the duration of the Gaussian-like analysis window. The pre-emphasis from (Hz) may be set at 50 so that frequencies below 50 Hz are not enhanced, frequencies around 100 Hz are amplified by 6 dB, and frequencies around 200 Hz are amplified by 12 dB, etc. This setting offsets the ~6 dB per octave attenuation seen in vowel spectra and creates a flatter spectrum that facilitates formant analysis (finding a local peak). The number of standard deviations may be set at 1.5, which is the number of standard deviations away from the mean where selective weighting of samples starts. The max number of iterations may be set at 5, which is first criterion for early stopping. The tolerance may be set at 1e-5, which is a second criterion for early stopping so that if the relative change in variance is less than tolerance, the refinement stops.

For example, speaker-specific LPC settings have been used to adapt the formant analysis to each speaker, with personalized settings estimated using an implementation of the Praat FastTrack plugin customized for the HTCondor framework on the OrangeGrid computing environment at Syracuse University during training of the machine learning algorithm. Formants may be estimated using the Praat Formant (robust) function with function calls automated using the Parselmouth API. Robust formants provide estimates using the autocorrelation method with robust linear prediction that is meant reduce variance and bias versus the Burg method of estimation. Five formants were estimated from 25 ms windows with a 25% overlap. Selective weighting of samples associated with the robust method began at 1.5 standard deviations with 5 refinement iterations. Formant value time series may be estimated for the entire word to minimize estimation error due to edge effects within the relatively short /ɹ/ intervals.

Useful settings for the Mel frequency cepstral coefficient extraction include extracting 12 coefficients from the audio. The time step(s) may be set at 0.005; the time between centers of consecutive analysis frames. The window length may be set at 0.025. The first filter frequency may be set to 100 Mels, with 100 Mel distance between the filters.

Useful settings for vocal tract gesture estimation include time step set to 0.02 (sampling at 50 Hz). The audio sampling rate may be 16,000 Hz. Useful pretrained models for feature extraction may include HuggingFace Wav2Vec2-large or HuBERT-large.

Spectral image information is generated through a series of Fast Fourier Transforms of the input signal. Useful settings for the Fast Fourier Transforms include a window length of 0.005 and time step at 0.002. The maximum analysis frequency may be 10,000 Hz. The frequency step may be 20 Hz. The shape of the analysis window is Gaussian.

Useful settings for HuggingFace Wav2Vec2 feature extraction include finalizing pre-training on an exemplary dataset, determining the section of the audio file associated with speech through voice activity detection, and requesting x-vector embeddings, and performing vocabulary adaptation. Hyperparameters for number of epochs, batch size, learning rate/learning rate scheduler, and the layers to unfreeze during pre-training may be tuned through an existing system such as Optuna.

Missing analysis samples for feature representations can imputed by mean-interpolation given the previous and following samples in the timeseries for that feature. System 10 may be further programmed to normalize the speech representation. For example, the speech representation may be z-standardized with regard to values for that representation from a correct speech sound from an age-and-sex matched individual from the training dataset.

System 10 may then use the frame-by-frame normalized temporal and spectral information as a feature matrix input to classifier 14 that comprises a machine learning algorithm that has been trained to detect and classify the relevant speech sounds.

The machine learning algorithm in classifier 14 may comprise a bidirectional long short-term memory recurrent neural network, convolutional neural networks, transformer neural networks, attention mechanisms, encoder/decoder neural networks, and temporal convolutional neural networks, random forest, or combination thereof. Frame-level predictions from the machine learning algorithm may be consolidated to a sound-level prediction by a metaclassifier comprising a bidirectional long short-term memory recurrent neural network, convolutional neural networks, transformer neural networks, attention mechanisms, encoder/decoder neural networks, and temporal convolutional neural networks, random forest, or combination thereof. For example, the PyTorch machine learning framework may be used for machine learning algorithm of classifier 14.

The algorithm of classifier 14 may consider Mel-frequency cepstral coefficients, formants/inter-formant distances, spectral image information, vocal tract gestures, and self-supervised learning speech x-vectors. Feature selection may then be used to reduce the number of independent variables. Feature selection also enables explainability as each feature/independent variable's importance is ranked according to its impact on the classification accuracy. Algorithm of classifier 14 may additionally consider models of voice activity detection, acoustic reverberation, deamplification, amplification, and background noise modeling to increase robustness of the final classifier to real-world acoustic conditions. The use of BorutaSHAP feature selection can help reduce overfitting by removing correlated features.

The training data used for system 10 should account for how both age and sex impact speech sound acoustics through their influence on vocal tract size and pitch. For example, a model trained on a large dataset (one model representing all available ages and sexes) can be compared to determine its impact on classification accuracy (F-metric) relative to a model trained with independent variable-adjusted acoustic features of a given participant dataset (one model representing all available ages and sexes) impacts classification accuracy (F-metric). In addition to the three formants, F1, F2, and F3, inter-formant distances, such as F3-F2, and deltas, training data may include speaker age and sex, exemplars from speakers matched on age and sex, as well as phonetic and phonological context.

Classifier 14 embedded in system 10 should account for how speech sound productions changes during treatment. System 10 may employ a series of classifiers personalized from classifier 14 to reflect a speaker's progress during treatment by fine-tuning the speaker-dependent model based on sound files produced by the speaker at the most recently completed speech therapy session. Speaker-independent classifier 14 may be made speaker-dependent (i.e., personalized) by taking audio recordings from a novel user not represented in the training set and extracting relevant speech features from audio in the manner described above. This audio may be collected by the fully computerized treatment program 12. The speaker-independent classifier 14 may be retrained with audio from the novel speaker in the manner consistent with its speaker-dependent training with the exception that a number of layers in the model will be unfrozen to allow the speaker-dependent classifier to update its training to most accurately analyze the speech from that speaker. This method may be performed weekly throughout the period of interaction with the fully computerized treatment program 12. In addition to the novel speaker, the speaker-dependent classifier training may include correct and mispronounced speech representations from age and sex matched speakers from the training dataset.

An exemplary dataset for training the speaker-independent classifier may comprise the desired sound tokens from 800 children, adolescents, and young adults ages 7-24, where each age band and sex may not be equally represented. Age and sex are two well-established factors influencing the acoustic structure of speech and may differently impact algorithm identification of the correct/incorrect speech sound tokens. Conventional deep learning approaches require a large dataset to optimize and capture the latent patterns and factors for effective and generalizable classification. Limitation of speakers (number of children)

present in the dataset may make require fine tuning on estimated vocal tract characteristics rather than age and sex.

Finally, system 10 provides a perceptual prediction output 26 reflecting the accuracy of the pronunciation of the target sound. Output 26 may comprise a binary decision, e.g., a bit indicating whether the pronunciation was correct. Output 26 could additionally include information about the reason why an incorrect decision was made for further use in training, e.g., output 26 may be provided as part of spoken and animated feedback returned to the learner so that speech motor chaining program 12 can automatically adapt practice trials to correct the specific problem leading to incorrect pronunciation.

In an embodiment of the present invention, system 10 containing a pilot speech analysis algorithm was trained on an audio corpus containing 179,076 correct and incorrect examples of /r/ from 351 children. Using common speech acoustic information, an embodiment of system 10 can classify previously unseen words (n=18.809) with a participant-specific accuracy (F-metric) of 0.81 relative to listeners' perceptual ratings.

What is claimed is:

1. A system for providing real-time detection and analysis of speech sounds to determine whether a predetermined sound in a word spoken by a patient has been correctly pronounced, comprising:

an input configured to receive an electronic audio file containing a target speech sound; and a processor coupled to the input and programmed to extract a set of acoustic features and a set of spectral features from the electronic audio file, wherein the spectral features include a plurality of formants and at least one inter-formant distance, wherein the processor is further programmed with a machine learning algorithm that has been trained with a predetermined data set to determine whether the target speech sound in the electronic audio file has been accurately pronounced and to output a signal reflecting the determination whether the target speech sound was accurately pronounced, wherein the machine learning algorithm is selected from the group consisting of a bidirectional long short-term memory recurrent neural network, convolutional neural networks, transformer neural networks, attention mechanisms, encoder/decoder neural networks, and temporal convolutional neural networks, and wherein the processor is further programmed to incorporate the determination whether the target speech sound was accurately pronounced into biofeedback for the patient when engaged in adaptive therapy in the absence of a clinician.

2. The system of claim 1, wherein the processor is further programmed to receive an audio file containing the target speech sound.

3. The system of claim 1, wherein the processor is further programmed to locate the target speech sound within the audio file.

4. The system of claim 1, wherein the processor is programmed to normalize the plurality of spectral features by z-standardizing according to age and sex specific format values.

5. The system of claim 1, wherein the machine learning algorithm comprises more than one algorithm selected from the group consisting of a bidirectional long short-term memory recurrent neural network, convolutional neural networks, transformer neural networks, attention mechanisms, encoder/decoder neural networks, and temporal convolutional neural networks.

6. The system of claim 5, wherein the processor is further programmed to perform feature selection of the plurality of spectral features to reduce a number of independent variables.

7. The system of claim 6, wherein the predetermined data set included a series of desired sound tokens from speakers having difference ages and different sexes.

8. A method of providing speech analysis to whether a predetermined sound in a word spoken by a patient has been correctly pronounced when the patient is engaged in adaptive therapy in the absence of a clinician, comprising the steps of:

receiving an electronic audio file containing a target speech sound;

processing the electronic audio file with a machine learning algorithm that has been trained with a predetermined data set to extract a set of acoustic features and a set of spectral features from the electronic audio file, wherein the spectral features include a plurality of formants and at least one inter-formant distance and the machine learning algorithm is selected from the group consisting of a bidirectional long short-term memory recurrent neural network, convolutional neural networks, transformer neural networks, attention mechanisms, encoder/decoder neural networks, and temporal convolutional neural networks, and to determine whether the target speech sound in the electronic audio file has been accurately pronounced;

outputting a signal reflecting the determination whether the target sound was accurately pronounced; and incorporating the determination whether the target speech sound was accurately pronounced into biofeedback for the patient in connection with adaptive therapy in the absence of the clinician.

9. The method of claim 8, further comprising the step of locating the target speech sound within the audio file.

10. The method of claim 8, wherein the machine learning algorithm comprises more than one algorithm selected from the group consisting of a bidirectional long short-term memory recurrent neural network, convolutional neural networks, transformer neural networks, attention mechanisms, encoder/decoder neural networks, and temporal convolutional neural networks.

11. The method of claim 10, further comprising the step of performing feature selection of the plurality of spectral features to reduce a number of independent variables.

12. The method of claim 11, wherein the predetermined data set includes a series of desired sound tokens from speakers having difference ages and different sexes.

* * * * *